United States Patent [19]

Hayenga et al.

[11] Patent Number: 4,935,354

[45] Date of Patent: * Jun. 19, 1990

[54] RENNIN FROM RECOMBINANT MICROBIAL CELLS FOR PREPARATION OF CHEESE

[75] Inventors: Kirk J. Hayenga, Burlingame; Virgil B. Lawlis, San Mateo, both of Calif.

[73] Assignee: Genentech, Inc., South San Francisco, Calif.

[*] Notice: The portion of the term of this patent subsequent to Apr. 23, 2002 has been disclaimed.

[21] Appl. No.: 927,778

[22] Filed: Nov. 5, 1986

Related U.S. Application Data

[63] Continuation of Ser. No. 513,883, Jul. 14, 1983, abandoned, which is a continuation-in-part of Ser. No. 452,227, Dec. 22, 1982, abandoned.

[51] Int. Cl.$^5$ ............... C12N 15/09; C12N 9/52; A23C 19/032; A23C 19/00
[52] U.S. Cl. .................. 435/69.1; 426/36; 435/71.2; 435/172.3; 435/220; 435/222; 435/224; 435/252.3; 435/252.31; 435/252.33; 935/14; 935/38; 935/60; 935/61; 935/73; 935/74
[58] Field of Search ............. 435/220, 222, 223, 224, 435/226, 68, 172.3, 254, 69.1, 71.2, 252.3, 252.31, 252.33; 426/36, 63; 935/14, 38, 61, 63, 64, 73, 74

[56] References Cited

U.S. PATENT DOCUMENTS

| | | | |
|---|---|---|---|
| 4,511,502 | 4/1985 | Builder et al. | 935/60 X |
| 4,511,503 | 4/1985 | Olson et al. | 435/172.3 X |
| 4,512,922 | 4/1985 | Jones et al. | 435/172.3 X |
| 4,518,526 | 5/1985 | Olson | 435/172.3 X |
| 4,666,847 | 5/1987 | Alford et al. | 935/14 X |

FOREIGN PATENT DOCUMENTS 8304418 12/1983 PCT Int'l Appl. .
2091271 7/1982 United Kingdom ......... 435/172.3 X

OTHER PUBLICATIONS

Goeddel, et al., Proc. Natl. Acad. Sci., vol. 76, No. 1, 1979, pp. 106–110.
Wetzel, et al., Biochemistry, vol. 19, 1980, pp. 6096–6104.
Williams, et al., Science, vol. 215, 2/1982, pp. 687–689.
Wetzel, et al., Gene, vol. 16, 1981, pp. 63–71.
Marston, A. O., Biochem. J., vol. 240, 1986, pp. 1–12.

*Primary Examiner*—David M. Naff
*Attorney, Agent, or Firm*—James G. Passé

[57] ABSTRACT

Rennin for making cheese is obtained from insoluble refractile bodies of a recombinant microbial host cell. The rennin is obtained by rupturing the recombinant host cell, isolating and solubilizing the insoluble refractile bodies, and recovering active rennin. Recombinant techniques involve preparing cDNA corresponding to the coding sequence for calf rennin, introducing into an expression vector and expressing in a host cell. As much as 200 mg rennin per liter of culture may be recovered. Prorennin or preprorennin may be produced and rennin derived therefrom.

6 Claims, 5 Drawing Sheets

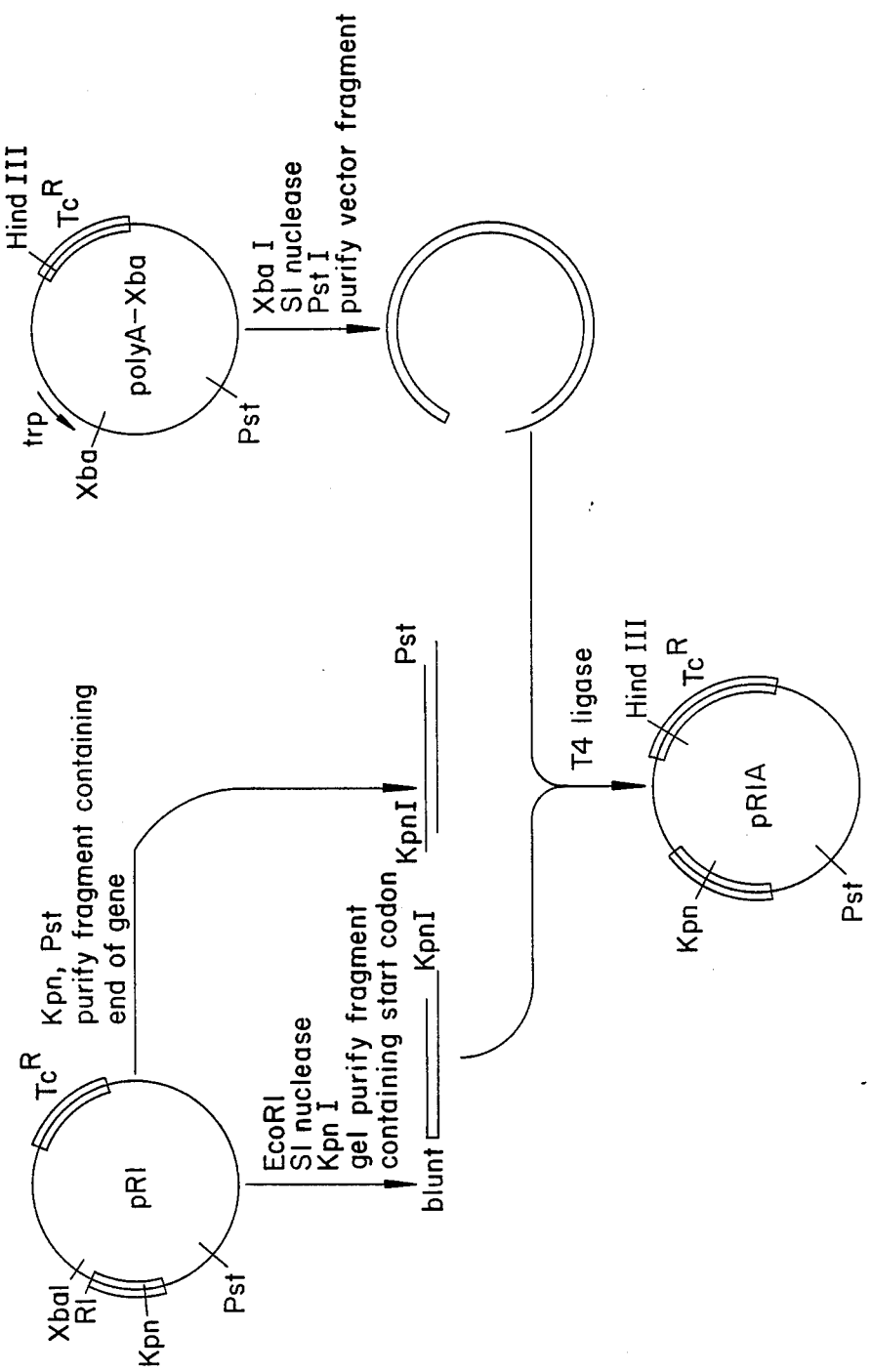

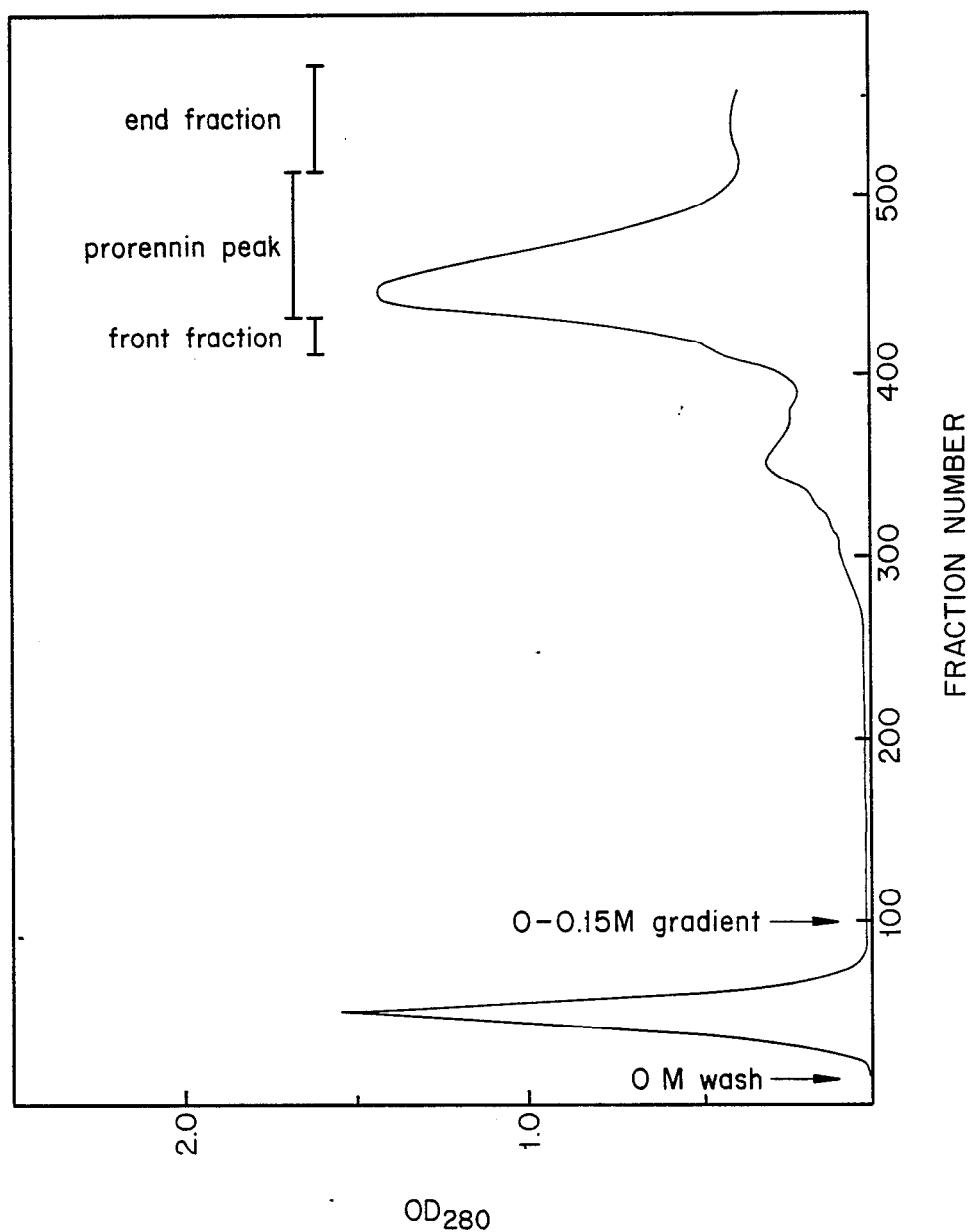

RENNIN FROM RECOMBINANT MICROBIAL CELLS FOR PREPARATION OF CHEESE

This is a continuation of U.S. Ser. No. 513,883 filed July 14, 1983, which is in turn a continuation-in-part of U.S. Ser. No. 452,227 filed Dec. 22, 1982, both now abandoned.

BACKGROUND

The present invention relates to the field of cheese production through the use of proteolytic enzymes, and in particular to the use of rennin, to coagulate milk. More specifically, the invention relates to producing rennin suitable for use in preparation of cheese, and to cheese production using rennin produced in microbial systems through the use of recombinant DNA techniques.

A. Cheese Production

The preparation of cheese has a long and venerable history. Basically, the preparation consists of the formation of solid curd which desirably includes milk fat, protein, and other insoluble salts in concentrated form, as well as sugar and soluble salts entrapped in a cheese serum included in the curd. In most cheeses, the precipitation and separation of the curd is followed by a ripening period wherein trapped living bacteria in the cheese milk carry out further metabolic reactions to impart distinctive flavors and texture characteristics.

In general, the coagulation is carried out in one of three ways. In cottage or cream cheese, the major protein constituent of milk, casein, is precipitated by acid, usually formed as a result of bacterial action, lowering the pH of the milk suspension to the isoelectric point. The pH at which precipitation occurs as a result of acid alone is reasonably low, pH about 4.7, and results in an overtone of sour taste. A second non-enzymatic precipitation method, used mainly to produce ricotta, utilizes a combination of high heat and medium acidity, about pH 6, to precipiate the curd. Finally, and most commonly, the standard Swiss, cheddar or provolone are precipitated at an elevated room temperature and at a reasonalby high pH, about 6.2, under the influence of a proteolytic enzyme. The most commonly used proteolytic enzyme is rennin, which has its origins, historically, in the use of cut strips of calves or lambs stomachs inserted directly into warm milk for coagulation into cheese as was done in ancient times. Later, European cheese making firms, learned to extract the stomachs of calves, kids and lambs to obtain a brown suspension or "rennet" used for cheese making. Present day rennet still comprises these extracts, but in a more purified form.

It will be obvious that such preparations present certain economic and practical difficulties. First, to obtain essentially pure rennet, the calves, lambs or kids must be milk fed, and less than two weeks old. Older offspring show the presence in the extracts of considerable amounts of pepsin in addition to rennin. Also religious restrictions in some areas of the world, such as India, prevent the butchering of the calves, and attempts have been made to obtain rennet directly through a fistula. All of the above approaches present sanitation and handling problems which require expenditure of considerable sums of money to solve. These difficulties have led to attempts to use substitutes such as swine pepsin (which makes the cheese bitter) and microbial proteases, such as those from *Mucor miehei, Bacillus cereus* or *Endothia parasiticus*, which appear to give satisfactory, but less desirable results than rennin. Also, plant extracts such as papain from the papaya tree, and bromelin from pineapple result in bitter cheeses. In summary, substitutes for purified calf rennin have had variable success in obtaining proper yields of curd, and the resulting cheese frequently has undesirable flavor characteristics.

Rennin coagulates milk at a desirable pH (6.4 to 6.0) and can be stored at low temperatures, and low pH, in the dark. It is now known that rennin cleaves the phenylalanine-methionine bond in kappa casein which thus destroys the casein's stabilizing action. Apparently, as a result of the cleavage, a glycomacropeptide soluble in whey is eliminated, and the remainder "para" kappa casein is itself coagulated in the presence of calcium ion to form an insoluble precipitate. Other casein forms which had been stabilized by kappa casein are then precipitated as well, also in combination with calcium ion. Removal of these proteins results in precipitation of still other components such as fats and insoluble salts. In short, apparently, kappa casein, a predominant milk protein is responsible for creating conditions which hold the other components of milk in more or less homogeneous suspension. If this casein is disrupted, the stabilizing influence is gone, and the remaining materials precipitate from solution. The manufacture of cheese by proteolytic enzymes capitalizes on this property of casein, in that any treatment of the starting material which results in the hydrolysis of casein provides the necessary environment for the formation of solids.

The enzyme above called "renin" is isolated from stomach mucosa at least partially in the form of its progenitor prorennin, which contains an additional 42 amino acids at the N-terminus. Rennin itself is composed of a single polypeptide chain of approximately 35,000 daltons molecular weight. Crude extracts of calf stomach mucosa contain some quantities of active rennin as well as the inactive precursor prorennin, which is converted to the active form at pH values below 5.

Production of rennin from calf stomach mucosa is costly, and limits the quantity of rennin available for the cheese industry. It would be desirable to obtain rennin, therefore, from a microbial source which can be grown at will and which lends itself to less costly processing requirements. Accordingly, it is the object of the present invention to provide such a dependable, reproducible and economic source of rennin using recombinant DNA techniques, and to utilize the rennin in the manufacture of cheese.

B. Recombinant Technology

The general aspects of DNA recombination and expression in host cells are now well understood. Briefly, the coding sequence for a desired protein is cloned to obtain sufficient quantity to work with, separated from contaminating sequences, and then inserted by known techniques into an expression vector which contains the necessary control systems, usually homologous to the potential host cell culture, to permit transcription into messenger RNA and translation into protein. To be practical, the expression vector must also contain a replication origin to permit it to replicate in the cell, either upon cell division or simply to amplify through reproduction in the non-dividing cell. The rennet utilized in the invention herein is produced by employing these techniques to provide a suitable expression vector for rennet in a microbial host, obtaining expression in this host, and recovering the rennet produced. This preparation can be used in the production of cheese according to the method of the invention.

SUMMARY OF THE INVENTION

The invention herein, in one aspect, is directed to a method for making cheese from milk using rennet produced by recombinant DNA techniques.

In the method of this aspect of invention, whole or skim milk is preincubated to a satisfactory temperature, usually in the upper room temperature range, and optionally supplied with a "starter" which comprises a bacterial culture which will be useful in the subsequent ripening of the cheese. To this preparation, is added an effective amount of rennet, which rennet has been prepared and recovered using recombinant DNA techniques and appropriate recovery procedures. After the formation of curd, the whey is separated, and the curd cut and allowed to heal, then cooked, and processed for consumption or ripening.

In another aspect, the invention is directed to a process for preparing useful quantities of rennet using recombinant techniques. In this aspect, cDNA is prepared corresponding to the coding sequence for rennet, introduced into an expression vector, expressed in a host cell, and recovered in active form. The invention is further directed to the expression vectors and transformed hosts useful in this method of rennet production, and to the rennet produced thereby.

Techniques are disclosed which permit the recovery of as much as 200 mg rennet per liter of culture, though even a production of 5 mg per liter would be useful. Alternatively, such production could be measured in terms of molecules per cell, or as equivalent of calf rennin activity.

BRIEF DESCRIPTION OF THE DRAWINGS

FIG. 1B is a schematic of the construction of plasmid pR1A.

FIG. 1D is a schematic of the construction of plasmid pR1AX.

FIG. 2 is the DEAE elution pattern for microbial prorennin (Ex 1, part C.8).

DETAILED DESCRIPTION

A. Definitions

Figure 1A:
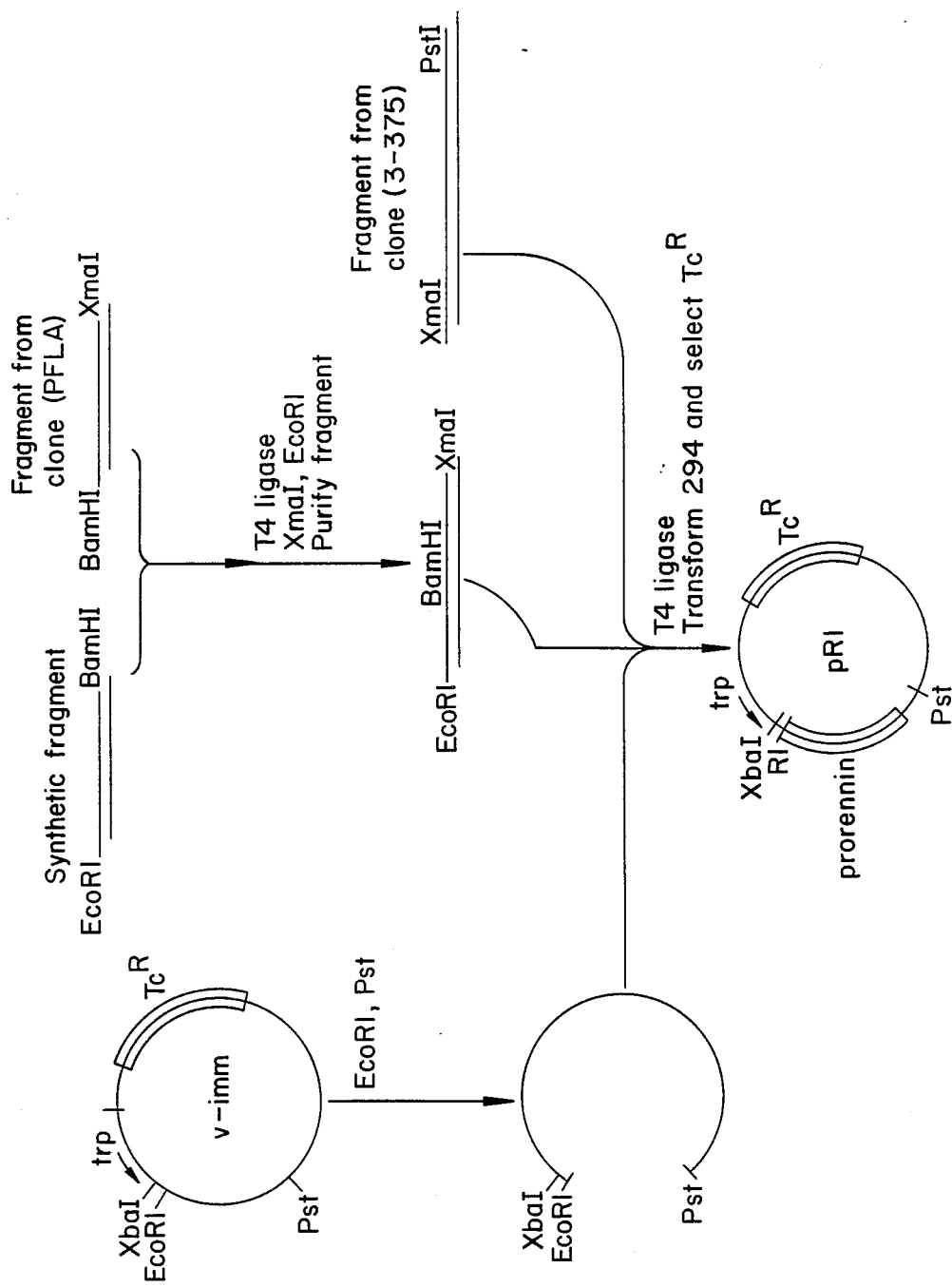
FIG. 1A is a schematic of the construction of plasmid pR1.

As used herein, microbial "rennet" refers to an enzyme preparation which is capable, after activation if necessary, of forming a cheese cord in milk utilizing the mechanism of isolated calf rennin—i.e. cleaving the phenylalanine/methionine linkage in casein type proteins. The definition of "rennet" thus includes proteins which are identical in amino acids sequence to calf rennin or its precursors, and those which are similar to it, though not identical, and which exhibit the same behavior. "Rennet" thus includes any "precursor" protein sequence which can be activated using conventional techniques to exhibit rennin activity. A classical example is that of prorennin, which is activated to rennin by treating the precursor at low pH. Preprorennin which contains an additional 16 amino acids at its N-terminus may similarly be activated by incubating at low pH values. Proteins functionally similar to prorennin and pre-prorennin are also included.

"Rennin" refers to a polypeptide which is substantially homologous with the sequence of amino acids found in the material isolated from calf stomach mucosa. It also includes, however, other proteolytic enzymes whose properties permit the same activity and specificity of the known amino acid sequence in calf rennin—i.e., cleavage of the phenylalanine/methionine linkage in proteins.

"Prorennin" refers to the amino acid sequence found in calf prorennin, but also includes similar polypeptides which are capable of being activated by pH values below 5 to form a protein which is capable of hydrolyzing proteins with the same specificity exhibited by rennin as herein defined. "Pre-prorennin" can also be so activated.

The amino acid sequences in both rennin, and its natural, inactive precursor, prorennin, are known. Rennin has a MW of approximately 35,000 and a sequence of 323 amino acids. Prorennin contains an additional 42 amino acids at the N-terminal end of the rennin molecule. Rennin itself, and therefore prorennin, exists naturally in two forms which differ only in the identity of the amino acid at position 286 of the prorennin molecule. In rennin A, and the corresponding prorennin, this amino acid is an aspartic acid residue, and in rennin B, and its corresponding prorennin, it is a glycine residue. Foltmann, B. et al. *Proc. Nat. Acad. Sci. (USA)*, 74: 2321 (1977) and *J. Biol. Chem*, 254: 8447 (1979). Both forms are equally active. In "pre-prorennin" an additional 16 amino acid sequence is attached to the N-terminal end of the prorennin.

B. General Description of the Cheesemaking Method

Successful cheesemaking may be judged by a number of criteria including yield, as measured by solids recovered, suitable bacterial content, and, or course, factors related to quality such as texture, flavor, color and palatibility. It is the object of the invention to provide a process for producing acceptable cheese on a practical scale using a milk clotting step which comprises use of rennet microbially produced in practical quantities.

In general the cheese making process of the invention utilizes either skim or whole milk of fat content suitable to the nature of the cheese desired. While unpasteurized milk may be used, pasteurized milk is preferred. Ordinarily, but optionally, a "starter" culture containing a bacterial strain which will be useful in ripening the cheese once the curd is formed is added prior to curd formation. While at the present time, the nature of the cheese ripening process is not entirely understood, it is certainly known that the resulting ripening, and the designation of cheese type, depends on the strain used as starter. In cheddar cheese, for example, the predominating bacteria are mesophilic lactic acid Streptococci, whereas in Swiss cheese, those predominating are thermophilic Streptococci and Lactobacilli. The ripening occurs over a period of a month or so or more, but the bacterial culture peaks about 24 hours after the formation of the curd. While bacteria can be supplied "naturally" from the milk itself in unpasteurized milk, or by accidental post contamination, usually they are supplied through purposely "starting" the cheese milk with pure cultures.

These cultures are most commonly S. lactis and L. bulgaris. strains ordinally found in milk, but which do not survive pasteurization. While generally undesirable, coliforms, including *E. coli* grow well in cold or warm cheese milk and in the curd as well. They produce gas in the cheese curd and encourage spoilage. While there is some thought that in certain types of fully ripened cheese, coliform bacteria aid in obtaining a typical flavor, *coli* typically are considered undesirable strains.

The process of preparing the milk, for example, through pasteurization or removal of fat, and the choice of starter culture if, indeed, any is used, do not form part of this invention. These are merely commonly used preparation procedures prior to adding a milk clotting enzyme to form the curd. In the process of the invention, the milk prepared as described above, is placed in vats of suitable size, and rennet, microbially prepared, is added at a rate to permit clotting which is sufficiently solid to permit cutting of the curd within 20 to 30 minutes. Shorter clotting times result in undesirable cheese qualities; longer clotting times, in addition to resulting in lower quality cheese, are relatively uneconomic. (The quantity of rennet to be added is determined by a small scale exemplar treated with the rennet preparation.) After clotting has occurred, the curd, cut into suitable size is treated by conventional means, including heating to perfect the clotting process, separation of whey, salting, hooping and pressing. The susequent precedures are variable depending on the form of the cheese desired, and are not a part of the invention.

In a typical process, raw milk is pasteurized at 140° to 170° F. for 30 minutes to an hour and then cooled. After a preincubation at approximately 86° F., a starter culture of, for example, *S. thermophillus* or *S. faecalis*, optionally containing, for example, *L. bulgaricus* or *L. helviticus*, or other suitable ripening bacteria, is added to approximately 1 percent of the milk weight. Thus, for a 400 pound vat, 4 pounds of starter culture would be added. In order to permit adequate proliferation of the culture, the milk is allowed to ripen at this elevated temperature for approximately an hour.

The rennet, which has been prepared from a microbial culture containing a suitable DNA sequence to express the appropriate enzymatic activity, is then added to the warm ripened milk. In a preferred embodiment, the quantity of enzyme added is judged by a preliminary small scale milk clotting experiment preparation, and chosen so that the milk is clotted sufficiently so that it can cut after 20 to 30 minutes, preferably about 25 minutes. After this time period, the curd is then cut, and allowed to heal for approximately 15 minutes before increasing the temperature to approximately 102° F. and allowing the pH to drop to approximately 6.1. Further reaction is encouraged by turning the curd periodically, for example, every 10 or 15 minutes. The pH continues to fall during this time to a pH of approximately 5.4 whereupon it is salted, hooped and pressed. Additional pressing is usually desirable. The resulting cheese is then aged in a cooler at approximately 40° F. under anerobic conditions. These conditions can be achieved by sealing the curd in a heat shrunk saran bag or by alternative provisions such as providing a $CO_2$ or nitrogen atmosphere.

C. Method for Production of Microbial Rennet

C.1 Outline of Procedure

The process of the invention whereby rennet is produced in commercially useful quantities using microbial systems may be outlined briefly as follows:

A. mRNA is isolated from a suitable source, such as calf, lamb or kid stomach, preferably calf fourth stomach mucosa. Of course, mRNA from any tissue which produces rennet will be an appropriate source. mRNA is conventionally separated from total cellular RNA using an oligo-dT column; however, any technique which is designed to segregate the mRNA from ribosomal and tRNA would fall within the scope of the invention.

B. Using conventional techniques, cDNA is prepared using the isolated mRNA as template and selected for that portion of mRNA which does for rennet sequences.

Briefly, the total, or partially fractionated, mRNA is treated with reverse transcriptase, primer, and a mixture of the four dNTPs in suitable buffer. RNA is removed using base, heat denaturing or other methods known in the art, and the complementary DNA strand formed by treating with appropriate enzymes, such as, for example, *E. coli* DNA polymerase 1, again in the presence of the 4 dNTPs and primer. (The polymerase enzyme may be added directly to the initial reaction mixture which contains these reagents.) The hairpin" in the resulting DNA is then cleaved by treating, for example, with SI nuclease.

The resulting mixture of double stranded DNA segments, after fractionation into those fragments of appropriate size by, for example, acrylamide gel electrophoresis, is then ligated into a cloning vector by providing suitable ligation sites on both the DNA fragments and on restriction endonuclease cleaved vectors. For example, a preferred method is to add poly C tails to the fragments and poly G tails to the cleaved vectors by treating with the appropriate dCTP or dGTP along with terminal transferase. Suitable cloning vectors are for example, endonuclease cleaved pBR322, pSC101, or pJC75-58, preferably pBR322.

The mixture of DNA fragments, thus annealed into cloning vectors, is used to transform competent cells by, for example, calcium treatment using calcium chloride (Cohen, S. N., et al, *Proc Natl. Acad. Sci. (USA)*, 69: 2110 (1972) and grown on a selective medium specific for a "marker" contained in the cloning vector. For example, if pBR322 is used, transformed cells will be ampicillin and tetracycline resistant, and only transformed cells will grow on media containing ampicillin or tetracycline. Transformed colonies are placed in microtiter dishes or other suitable containers which will permit retention of a viable colony sample, while permitting assay for presence of the desired DNA sequence.

Typically, selection of the desired clones if effected by transferring an imprint of the colonies onto nitrocellulose and treating the resulting replica with a solution containing a suitable probe. Suitable probes comprise radioactivity or fluorescent labeled compounds specific for the desired DNA sequence. In the present invention, as the amino acid sequence of rennin is known, synthetic nucleotide sequences which would code for this result may be used, as may DNA fragments isolated from previous cloning and selection processes.

The selected colonies provide plasmids with the desired sequences, which sequences can be recovered by suitable digestion with restriction endonucleases. Techniques for recovering plasmids from cell cultures, for mapping their DNA inserts and for recovery of the desired sequences are well known in the art. Briefly, the isolated plasmids are analyzed by acrylamide gel electophoresis of fragments resulting from double digests using restriction enzymes. By accumulation and analysis of data derived from this process, along with the known restriction enzyme specificities, sizable portions of the gene are recoverable from the transformed colonies.

C. The fragments are then pieced together to form the complete coding sequence and expressed in host cells. These fragments can, with appropriate tailoring as necessary, be ligated into plasmids containing promoter-operon and replication sites. When used to transform appropriate host cell cultures, these plasmids result in expression of the desired sequence by the transformed organism.

D. The resulting protein having the properties of rennet is then recovered from the host cell culture using techniques which are successful in correct management of the 3-dimensional structure of the enzyme.

C.2 Level of Production

By utilizing the foregoing techniques, rennet is produced in host cell cultures in sufficient amounts to be useful in the clotting of milk for cheese making. Production of 5 mg of rennet per liter of cell culture provides activity sufficient to clot milk effectively, but amounts over 200 mg per liter are producible by the method of the invention. Amounts produced may be measured by assaying the recovered protein according to expected molecular weight or by reactivity with appropriate antibody preparations. A particularly useful assay is that for milk clotting activity, either by measuring the clot diameter on plates, as described by Sokol, et al, *J. Clin. Microbiol.*, 9: 538 (1979) or by time required to clot liquid milk samples as described in *First Supplement of Food Chemicals Codes*, 2nd Ed., p. 84. Using such activity as a criterion, amounts of rennet, particularly as prorennin, equivalent in activity (when activated if necessary) to that exhibited by 5 mg purified calf rennin to more than 200 mg are produced per liter of host cell culture.

Alternatively, the aforementioned amounts may be ascertained in terms of molecules produced per cell (as judged either by measurement of quantity, antibody reaction or activity in milk clotting). Using the method of the present invention $10^3$ to more than $4 \times 10^4$ molecules per cell are produced.

C.3 Preferred Embodiment

In a preferred embodiment of the present invention, the foregoing procedure was applied as follows:

mRNA isolated from the fourth stomach mucosa of calves and purified on an oligo-DT column is used to prepare cDNA. Based upon information developed in the context of the present invention, a preferred primer in the synthesis of cDNA is dGATCCCGT-GAATTCGG. The resulting cDNA is subjected to acrylamide gel electrophoresis, and the fragments containing more than 1,000 base pairs are recovered. The mixture of these fragments is then tailed with poly C, and annealed into Pst 1 cleaved pBR 322 which has been tailed with poly G. The cloning vector mixture is transformed into a suitable host such as *E. coli*, and transformed cells detected by growth on tetracycline containing medium. The resulting colonies are probed with both Tth probe, described hereinbelow, or with the aforementioned synthetic primer. From the colonies thus selected, plasmids are isolated and the 440 base pair segment between the Bam H1 and Xma sites is recovered and isolated. This is ligated to a synthetic cDNA fragment containing the ATG start codon, preceded by an Eco R1 cleavage site, and the codons for the first four amino acids in prorennin. The construction of this synthetic fragment is described hereinbelow. This fragment is ligated to an 800 base pair fragment bracketed by the XmaI and Pst I cleavage sites of a similarly constructed DNA fragment containing cloning vector derived from cloned *E. coli* using the procedure outlined above except that oligo dT is used as primer and a synthetic pool of 4 sequence described hereinbelow is used as probe. Colonies thus selected, after sequencing, are used as the source of the 800 base pair segment described. The resulting DNA fragment is then ligated in an expression plasmid derived from γ-IMM, also described below, double digested with EcoR I-Pst I. The resulting plasmid is used to transform *E. coli* W3110 (F−, λ−, prototrophic, ATCC 27325) or other appropriate microbe. The cells are grown on LB growth medium containing tetracycline, and induced by addition of indole acrylic acid. The cells are harvested and the presence of prorennin analyzed for as described below.

When grown as thus described, prorennin is precipitated within the cell. The prorennin is recovered by solubilizing it in a denaturing solution, for example 5M guanidine HCl. The solubilized prorennin is then sulfonated using a sulfite solution in the presence of a mild oxidizing agent, buffer exchanged with urea, purified on DEAE cellulose and diafiltered into redox buffer containing reduced (predominantly) and oxidized glutathione. The resulting protein solution is then activated for use in cheese production by treating with acid at pH 2.

C.4 Suitable Host Cells and Vectors

Preferred embodiments of suitable host cells for production of rennet include *E. coli*, *B. subtillis*, and yeast, although any microbial host cell system may be used. The following sets forth the parameters affecting the use of various such cultures:

The work, described in Example 1 hereinbelow, employed for cloning purposes, *E. coli* K12 strain 294 ATCC number 31446. Expression was obtained using *E. coli* W3110 (F−, λ−, prototrophic), ATCC 27325. However, various other microbial strains are useful, including known *E. coli* strains such as *E. coli* B, and *E. coli* X1776 (ATCC No. 31537, deposited July 3, 1979) or other microbial strains, many of which are deposited and available from recognized microorganism depository institutions such as the American Type Culture Collection (ATCC). For example, bacilli, such as *Bacillis subtilus* and other enterobacteriaceace, such as *Salmonella typhimurium* or *Serratia marcesans*, or various Pseudomonas species may also be employed.

Prokaryotic systems are transformed for expression by employing a plasmid vector containing a replicon and control sequences which are derived from the species compatible with the host cell. For example, *E. coli* is typically transformed using pBR 322, a plasmid derived from an *E. coli* species (Bolivar, et al., *Gene* 2: 95 (1977)). This vector ordinarily carries a replication site, as well as marking sequences which are capable of providing phenotypic selection in transformed cells. pBR322 contains genes for ampicillin and tetracycline resistance and thus provides an easy means for identifying transformed cells. The pBR322 plasmid, or other microbial plasmid must contain or be modified to contain promoters which can be used by the microbial organism for expression of its own proteins. Those promoters most commonly used in recombinant DNA construction include the β-lactamase (penicillinase) and lactose promoter systems (Chang et al., *Nature* 275: 615 (1978); Itakura, et al., *Science,* 198: 1056 (1977), (Goedell, et al. *Nature* 281: 544 (1979)) and a tryptophan (trp) promoter system (Goeddel, et al., *Nucleic Acids Res.,* 8: 4057 (1980); EPO Appl Publ No. 0036776). While these are the most commonly used, other microbial promoters have been discovered and utilized, and details concerning their necleotide sequences have been published, enabling a skilled worker to ligate them functionally with plasmid vectors (Siebenlist, et al. *Cell* 20: 269 (1980)).

In addition to prokaryotes, yeast cultures may also be used. *Saccharomyces cerevisiae,* or common baker's yeast is the most commonly used among eukaryotic microorganisms, although other commonly available strains of yeast may also be used. For expression in Saccharomyces, the plasmid YRp7, for example, (Stinchicomb, et al. *Nature,* 282: 39 (1979); Kingsman et al., *Gene,* 7: 141 (1979); Tschemper, et al., *Gene,* 10: 157 (1980)) is commonly used. This plasmid already contains the TRP1 gene which provides a selection marker for a mutant strain of yeast lacking the ability to grow in tryptophan, for example ATCC No. 44076 or PEP4-1 (Jones, *Genetics,* 85: 12 (1977)). The presence of the trp1 as a characteristic of the yeast host cell then provides an effective environment for detecting trp1 transformation by growth in the absence of tryptophan.

Suitable promoting sequences in yeast vectors include the promoters for 3-phosphoglycerate kinase (Hitzeman, et al., *J. Biol. Chem.* 255: 2073 (1980)) or other glycolytic enzymes (Hess, et al., *J. Adv. Enzyme Reg.* 7: 149 (1968); Holland, et al., *Biochemistry,* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing the expression plasmid of the invention, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast compatible promoter, origin of replication and termination sequences may be used.

D. EXAMPLES

The following examples are intended to illustrate but not to limit the invention.

EXAMPLE 1

Preparation of Practical Quantities of Microbial Calf Prorennin

The following preparation is exemplary of successful processes which permit preparation of rennet suitable for use in the process of the invention. Other host organisms, procedures for preparing the correct DNA sequences, and for producing expression vectors are entirely consistent with preparing rennet which may be used in the process of the invention. The particular example given relates to the production of prorennin from *E. coli.* However, other host organisms and other rennet forms such as rennin or pre-prorennin are within the scope of the invention.

a. Isolation of Messenger RNA for Prorennin

The fourth stomachs of freshly slaughtered calves of less than one week of age were removed and transported on ice from Conti Meat Packing Company, Inc., Henrietta, N.Y., and the mucosa promptly dissected away from the supporting tissue.

Polysomes were isolated from 217 grams of mucosa by the method of Palmiter, R. D., *Biochemistry,* 13: 3606 (1974), incorporated herein by reference, except: solutions were autoclaved for one half hour; tissue was homogenized with a phenol washed Brinkmann homogenizer (Polytron Model PT10ST), and polysomes were pelleted through 1M sucrose in PB (polysome buffer) in heat sterilized 250 ml Nalgene polycarbonate tubes.

The polysomes were then resuspended in 90 mls of 0.05M Tris, pH 7.2 plus 10 ml of Tenex extraction buffer (Tenex is 50 mM Tris, pH 7.0, 500 mM NaCl, 250 mM EDTA, 5 percent SDS), and the solution heated to 65° C.

Protein was removed by centrifugation at low speed to remove debris, followed by addition of 40 mg of *Tritirachium aulbum* proteinase K, bound to SAH-cellulose (MCB-EM reagent from MCB Manufacturing Chemists, Incorporated, Gibtown, N.J.). The mixture was incubated for one hour at 25° C. with shaking, and the proteinase K-cellulose removed by centrifugation. The supernatant was extracted with an equal volume of 50:50 v/v phenol:chloroform. The mixture was centrifuged, and the aqueous phase extracted once with chloroform, and the organic layer plus interphase bulk extracted with 20 ml of 0.02M Tris, pH 7.2. The aqueous phases were combined and 0.1 volumes of 2M sodium acetate, pH 5.5, and two volumes of ethanol were added. The RNA was allowed to precipitate in storage at −80° C., and collected by centrifugation at 12,000×g, lyophilized to remove residual ethanol, and redissolved in 10 mM Tris, 1 mM EDTA, pH 7.5.

This RNA solution was adjusted to an RNA concentration of about 2 mg per ml by diluting with 10 mM Tris, pH 7.4, 1 mM EDTA, 0.2 percent SDS, and 0.5M NaCl, and passed over a column of oligo-dT-cellulose (Type 3, Collaborative Research, Lexington, Mass.) which had been prepared in 1.5 cm diameter sterile econo columns (Bio Rad Laboratories, Richmond, CA). The flow through was recycled over the column twice again. The column was then washed with binding buffer plus SDS until no UV absorbing material eluted as monitored by passing the eluate through a precision type 513 ultramicro continuous Quarasil flow cell in a Beckman L-25K spectrophotometer. The bound RNA was then removed from the column by washing with an elution buffer which had been warmed to 65° C. and the eluate was collected in 2.5 ml fractions in sterile siliconized 13×100 borosilicate tubes using a Gilson microfractionator. The mRNA containing fractions were recycled over the oligo dT columns twice to achieve further purification of poly A messenger. The resulting poly A messenger fractions were brought to 0.2M in potassium acetate and precipitated with 2 volumes of ethanol and the precipitate stored at −80° C. This mRNA, unfractionated, was used to prepare cDNA as described below.

b. Materials and Methods for Construction of Expression Plasmids Incorporating Sequences from mRNA Unless otherwise specified, the procedures used in the description herein are as follows:

b.1 Preparation of cDNA from mRNA

The procedure is as described in Goeddel D. et al., *Nucleic Acids Research*, 8: 4057 (1980), incorporated herein by reference, and was applied with results subsequently to be described.

Briefly, for 100 μg mRNA, the initial $^{32}P$ labeled single strand DNA was formed by placing the unfractionated mRNA, prepared as described above, in 100 μl of reverse transcriptase buffer solution (20 mM Tris, pH 8.3, 20 mM KCl, 8 mM MgCl$_2$, 30 mM BMSH) which is 1 mM each in the four dNTPs, (100 microcuries $^{32}P$ dCTP), and contains approximately 2 μg primer, 100 units RNAsin (Biotech) (an RNAase inhibitor) and 160 units of reverse transcriptase. The solution was incubated at 42° C. for 30 minutes; then quenched in ice water and boiled for 3 minutes. After cooling, denatured protein was removed by centrifugation, and the supernatant recovered.

The complementary DNA chain was then formed by adding an equal volume of ½ times reverse transcriptase buffer with 10 units DNA polymerase Klenow fragment (Biolabs) and incubated at 14° C. for 3 hours. Reaction was stopped and protein extracted by vortexing with 100 μl of phenol saturated with buffer (5 mM Tris, pH 8, 200 mM NaCl, 1 mM EDTA) and adding 100 μl chloroform. The aqueous phase was then removed and the nucleic acid precipitated with 2.5 times the volume of ethanol at −20° C. The precipitate was spun down and washed with cold 70 percent ethanol. The foregoing method of protein removal by phenol chloroform and nucleic acid recovery by ethanol precipitation was followed throughout.

The pellet was then dissolved in 100 μl SI buffer (25 mM NaOAc, pH 4.5, 1 mM ZnCl$_2$, 300 mM NaCl) and treated with 800 units SI nuclease (Miles) at 37° C. for 90 minutes to cleave the "hairpin" in the cDNA.

The mixture was then phenol-chloroform extracted as above set forth and nucleic acids precipitated using 4 volumes ethanol at dry ice temperatures.

The pellet was resuspended in 45 μl TEB and 5 μl 50 percent glycerol, 0.1 percent X C, 0.1 percent BPB added. The solution was loaded onto 6 percent acrylamide gel prepared as described in Goeddel (supra) (5 ml 10x TEB, 2 ml 1.6 percent APS, 7.5 ml 40 percent acrylamide, 36 ml water, 50 μl TEMED.) After 30 minutes at 300 volts the gel was cut and stained in EB to determine size locations. (Acrylamide gel electrophoresis was run in the foregoing manner throughout.) The band corresponding to the desired size was counted using Cerenkov counts and electroeluted into about 300 μl 1/10 TEB buffer and recounted to determined yield of cDNA. The volume was reduced to 200 μl, to this was added 20 μl 3M NaOAc, pH 4.8 and 550 μl cooled ethanol. This cDNA was stored at −20° C.

b.2 Colony Library Preparation 20 ng (as judged by recovered radioactivity) of the cDNA as prepared in paragraph b.1 was tailed with poly C as follows:

To 20 ng cDNA, suspended in 10 μl water, were added 10 μl of 10x cacodyalate buffer, 10 μl 10 mM dCTP, 68 μl water, 1 μl 100 mM CoCl$_2$, and 100 units terminal transferase. The mixture was incubated at 37° C. for 5 minutes and protein removed by phenol-chloroform extraction as described above. To supernatant was added 0.8 ng PstI cleaved pBR322 tailed with poly G, along with 10 μl 3 mM NaOAc, pH 4.8, and 275 μl ethanol. The spun down (nucleic acid) precipitate was resuspended in 360 μl water plus 40 ‖ 1 10x annealing buffer (100 mM Tris, pH 7.5, 2.5 mM EDTA, 1M NaCl) and incubated at 70° C. diminishing to 37° C. overnight.

200 μl of the annealed vectors thus prepared were used to transform 400 μl of *E. coli* K12 strain 294 cells, ATCC 31466 by treating with calcium ion (calcium chloride solution). After 1 hour, the cells were heat shocked at 42° C. for 70 seconds and held for 90 minutes in 5 ml LB. 400 μl of cell culture was then plated onto 12 large plates of LB containing 5 μg/μl Tc, and the transformed colonies were recovered.

The colonies were picked into microtiter dishes, incubated overnight, and stamped onto nitrocellulose filters (BA85) placed on LB plates containing 5 μg per μl Tc. The remaining portions of the colonies in the microtitered dishes were preserved by adding 25 μl of 42 percent DMSO and storing at −20° C.

The transferred portions of the colonies were incubated for 8 to 9 hours at 37° C. and amplified by transferring the filters to plates containing 12.5 μg/ml chloramphenicol and incubating at 37° C. overnight.

Each nitrocellulose filter containing transformed, cultured, and amplified colonies was probed for the desired cDNA sequence as follows:

Each filter was floated successively on a lysis solution (0.5M NaOH, 1.5M NaCl) for 3 minutes, on a neutralizing solution (0.5M Tris, 3M NaCl pH 7.5) for 15 minutes and on 2×SSC solution for 15 minutes and then dried.

In the meantime, kinased probe (described below) was prepared by the method of Goeddel, et al., *Proc. Nat. Acad. Sci.*, 76: 106 (1979), incorporated herein by reference. 100 pmol of DNA probe was treated in kinase buffer (60 mM Tris, pH 8, 10 mM MgCl$_2$, 10 mM BME) with 25 μl $^{32}P$-ATP and 10 units of T4 kinase (BRL) for 30 minutes at 37° C. Labelled probe was separated from unincorporated $^{32}P$ using a G-50 column.

The dried filters described above were prehybridized by covering them with a solution of the following composition: 400 ml solution contained 72 ml 5M NaCl, 40 ml 50x Denhardt (50x Denhardt=1 percent each bovine serum albumin, polyvinylpyrrolidine (PVP), and SDS), 20 ml 10 percent NP40, 80 mg sonicated salmon sperm DNA, 36 ml 1M Tris, pH 7.5, and 9.6 ml of 250 mM EDTA.

Labelled probe was then added and the filters were incubated at 37° C. overnight. The filters were washed with 6×SSC with 0.1 percent SDS, dried, and placed against photographic film to locate colonies containing $^{32}P$-i.e., those which are hybridized with probe.

b.3 Isolation of cDNA Plasmids and Sequence Analysis

Plasmids were isolated from the identified cultures using the cleared lysate method of Clewell, D. B. and Helinski, *Biochemistry* 9: 4428 (1970), incorporated herein by reference, and purified by column chromatography on Biorad A-50 Agarose. Smaller amounts (minipreps) were prepared using the procedure of Birnboim, H. C. *Nucleic Acids Research*, 7: 1513 (1979).

Fragments of the cloned cDNA containing plasmids were prepared for sequencing by treating about 20 μg of plasmids with 10 to 50 units of the appropriate restriction enzyme or sequence of restriction enzymes in approximately 600 μl solution containing the appropriate buffer for the restriction enzyme used (or sequence of buffers); each enzyme incubation was at 37° C. for one hour. After incubation with each enzyme, protein was removed and nucleic acids recovered by the phenol-chloroform extraction and ethanol precipitation as set forth above.

After cleavage, the preparation was treated for one hour at 37° C. with 10 units Klenow in 100 μl of Klenow buffer (50 mM KPi, pH 7.5, 7 mM MgCl$_2$, 1 mM BME), containing 50 nmol dNTP. Protein was removed and nucleic acids recovered as above, and the nucleic acids suspended in 40 μl of loading buffer for loading onto 6 percent polyacrylimide gel, as described above, for sizing.

DNA sequencing was performed by the M—vector method (Messing, et al, *Nucleic Acids Research*, 9: 309 (1981) or by the method Maxam, et al, *Methods in Enzymology*, 65: 499 (1980).

b.4 Ligation Procedures

DNA fragments, including cleaved expression plasmids were ligated by mixing the desired components (e.g. vector fragment cut from 0.25 μg plasmid is mixed with insert cut from 1 μg of plasmid in 20 μl reaction mixture), which components were suitably end tailored to provide correct matching, with T4 DNA ligase. Approximately 10 units ligase were required for μl quantities of vector and insert components. The resulting plasmid vectors were then cloned by transforming *E. coli* K12 strain 294 (ATCC 31446). The transformation and cloning, and selection of transformed colonies were carried out as described above. Presence of the desired sequence was confirmed by isolation of the plasmids from selected colonies, and DNA sequencing as described above.

b.5 Additional Literature References:

Additional procedures for preparation of cDNA may be found in Goeddel, et al, *Nature*, 287: 411 (1980); Goeddel, et al, *Nature*, 281: 544 (1979); Wickens, et, al, *J. Biol Chem*, 253: 2483 (1978).

c. Prorennin Expression c.1 Preparation of Probes for Initial Cloning of the Prorennin in Sequence

Three types of probes were prepared as follows:
Four synthetic DNA sequences dTTCATCAT(-G$^4$)TT(G$^4$)TC were prepared by the method of Crea, R. and Horn, T., *Nucleic Acids Res.*, 8: 2231 (1980) except that 2,4,6-triisopropyl benzene sulfonyl-3-nitro-1,2,4-triazole (TPS-NT) was used as coupling agent (de Rooij, J. F. M. et al., *Rec. Trav. Chin. Pays-Bas*, 98: 537 (1979)). This set of probes will be referred to herein as the "probe mixture".

The sequence dGATCCGTCGAATTCGG, hereinafter called "primer/probe" was also prepared synthetically and utilized as indicated hereinbelow.

A third "Tth probe" was constructed by recovering and cloning the sequence between two Tth 111 I cleavage sites in a cloned plasmid derived from unfractionated mRNA. In preparing this probe, 100 μl of unfractionated mRNA, prepared as described above was converted to cDNA, cloned, the plasmids recovered and the probe excised by treating with Tth 111 I. In this preparation, oligo-dT (12-18) was used as primer in the initial reverse transcriptase reaction; the cDNA was size separated on 6 percent acrylamide gel, and the fraction containing greater than 1000 base pairs was recovered for annealing into the cloning vector. Upon transforming *E. coli* 294, 800 transformed colonies were obtained, and one of them, 4H10, hybridized with "probe mixture". Plasmids were isolated from the 4H10 culture, and t7h111 I digestion carried out as described above. The fragments were subjected to gel elecrophoresis as described above, and the 320 base pair Tth 111 I "small" fragment electroeluted and labeled by boiling with 2 μl (1 μg) of calf thymus primer in 28 μl of water for 4 minutes, and adding the boiled solution to a tube containing 13 μl of α-$^{32}$PdCTP (130 μCi) (New England Nuclear), 9 μl 0.1 mM dGTP, dATP, dTTP, and 6 μl of 10x buffer (10x buffer refers to 60 mM NaCl, 60 mM MgCl$_2$, 60 mM Tris, pH 7.5, 50 mM DTT). The reaction mixture was incubated at room temperature for 1½ hours, and added to 40 μl of 20 percent glycerol, 0.05 percent SDS, 20 mM BBA, and loaded onto a G50 column to remove unincorporated nucleotides. The resulting labeled preparation was used as the "Tth probe".

c.2 Preparation of Prorennin Sequences

The prorennin gene for insertion into an expression plasmid was derived from a fragment at the 5' end ligated to a 3' end fragment. These were prepared as follows:

The 5' end fragment was a ligation of a synthetic fragment and a fragment derived from clone PFLA, as described below. The synthetic fragment has the structure:

```
                [Met] [Ala] [Glu] [Ile] [Thr]
d A A T T C A T G G C A G A A A T A A C A A G
            G T A C C G T C T T T A T T G T T C C T A G d
```
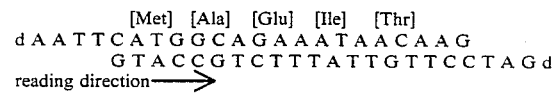

This sequence contains an EcoRI site at the "upstream end" an ATG start codon, followed by sequences coding for the first four amino acids in prorennin, and terminates ina BamH1 site.

The cloned fragment to which this synthetic fragment is ligated in order to form the 5' end of the gene comprises a Xma-BamHI fragment of approximately 440 base pairs derived from the 5' end of the gene.

The appropriate 440 bp fragment was obtained from cDNA derived from unfractionated mRNA as described above, using as primer, dGATCCGTCGAATTCGG, i.e., the "primer probe". The cDNA formed using this primer was size fractionated as set forth above and fragments having more 1,000 base pairs inserted into the PstI site of pBR322 for cloning. The resulting clones were selected using both Tth probe and the primer/probe as probes. Only colonies hybridizing with both were selected. From 1,280 transformed colonies, about 300 colonies were obtained which showed hybridization with both probes. These were examined for presence of the 5' portion of the prorennin sequence as follows:

The results of a series of double digestions using Ava I-Pvu I, AvaI-BamH I, Bgl I-BamH I, and Bgl I-EcoR I were analyzed. Advantage was thus taken of the known Pvu I and Bgl I sites, each 125 base pairs either side of the pBR322 Pst site utilized for insertion of the cDNA sequence. These digestions provide suitable fragments for analysis. A rough map of the appropriate fragment as it is disposed in the PstI site of pBR 322 is shown below.

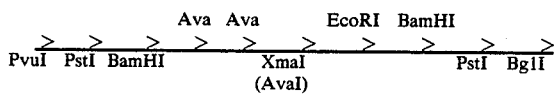

The desired clone, PFLA, was selected by analysis of acrylamide gel electrophoresis performed on the above double digests of mini preps prepared from the identified clones. Plasmids were then isolated from PFLA clone, double digested with BamH I and XmaI, and the 440 bp fragment recovered by gel electrophoresis.

The "complete" 5' end was then created by a standard ligation reaction utilizing the synthetic fragment and the PFLA clone BamHI-XmaI fragment with T4 ligase followed by cleavage with XmaI and EcoRI. The resulting ligated sequences were purified on acrylamide gel electrophoresis selecting for the appropriate 455 base pair fragment.

The 3' end fragment was prepared in an manner analogous to that used to prepare the PFLA clone. cDNA containing >1000 bp formed from unfractionated messenger RNA using oligo-dT as primer, was cloned as above, and colonies selected with Tth probe. Approximately 50 colonies resulted. The desired clone was selected by analyzing the results of gel electrophoresis formed on plasmid minipreps which were double digested with BamHI/BglI, PvuI/BamHI, EcoR1/BglI, and PvuI/EcoR I again taking advantage of the PvuI and BglI sites flanking the PstI insert site. The plasmids from the desired colony were isolated, then cleaved with Xma I and Pst I, and electophoresed to isolate the 800 bp sequence of the "3-375" fragment shown in FIG. 1A. The "3-375" fragment extends from the Xma site congruent with that from the PFLA fragment, past the end of the gene to the Pst I insertion site. An approximate map of this fragment as it is deployed in the PstI site of pBR322 is shown below.

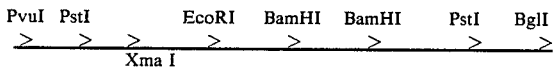

c.3 Construction of the Expression Plasmid pR1

FIG. 1A outlines the construction of the initial plasmid used for prorennin expression. Advantage is taken of a hybrid gene at the 5' end in which the section coding for the N-terminal portion of the prorennin is made synthetically, thus allowing the incorporation of an ATG initiation codon for protein synthesis in front of the triplet coding for the first amino acid.

The prorennin expression plasmid pR1 was constructed by incubating EcoR1-Pst I cleaved γ-IMM plasmid with the 5' and 3' segments constructed as described above in the presence of T4 ligase. (γ-IMM, is a pBR 322 derived plasmid, the construction of which is essentially that described for pIFN-γ trp 48 in U.S. application Ser. No. 312,489, filed Oct. 19, 1981, incorporated herein by reference and by Gray et al., Nature, 295: 503 (1982). Specifically, γ-IMM differs from pIFN-γ trp 48 by one base pair so as to contain an XbaI site contiguous to the EcoRI site downstream from the trp promoter. The XbaI site unaccountably lost in the construction of pIFN-γ trp 48 there described can be introduced by replacement of the ca. 40 bp sequence spanning the HpaI (within the trp promoter) to EcoRI site of pIFN-γ trp 48 with a corresponding ca. 40 bp HpaI to EcoRI sequence having an XbaI site contiguous to the EcoRI site, prepared by suitable digestion of pLeIFA25 (Goeddel et al., Nature, 287: 411 (1980) or pHKY1 (European Patent Application Publication No. 0036776).)

Alternatively, pIFN-γ trp 48 can be modified to provide the Xba I site by digestion with EcoRI and ligation to the EcoRI-EcoRI trp promoter/operator fragment described in EPO Publn. No. 0036776 (supra) to give an intermediate plasmid, 48-13, containing tandem trp promoter/operators. Plasmid 48-13 is then digested with HpaI and religated.

The ligation mixture was used to transform E. coli K12 294. Plasmids were isolated from the selected transformed clones, and one was selected for sequence to confirm the proper junction of the desired fragments.

c.4 Expression of Prorennin

E. coli K12 (294/pR1) was inoculated into a test tube containing 5 ml LB growth medium containing 5 μg/ml tetracycline. The cells were grown overnight at 37° C. An aliquot of this culture was diluted 1:150 into 60 mls of M9 medium containing 5 μg/ml tetracycline. The cells were grown in a shaker flask at 37° C. for 4 hours, to a resulting absorbance at 550 nm of 0.25 and the tryptophan analog, indole acrylic acid, added to a concentration of 20 μg/ml. The cells were incubated 70 minutes, to an absorbance at 550 nm of 0.5 and harvested by centrifugation. The cells were resuspended in 0.7 ml of phosphate buffered saline containing BSA. The resulting suspension was sonicated and assayed for the presence of prorennin by concentrating the suspension and subjecting the concentrate to SDS PAGE, according to the method of Laemmli, Nature, 227: 680 (1970), incorporated herein by reference. The slab gel was electrophoretically transfered to nitrocellulose paper in the presence of 20 mM tris, 200 mM glycine, pH 8.5 at 1 m amp for 90 minutes. Removal of the protein from the slab gel was verified by staining with Coomassie blue.

The nitrocellulose paper was then rinsed briefly in water and incubated in 100 μl NET buffer (50 mM Tris, pH 7.4, 0.15M NaCl, 5 mM EDTA, 0.25 percent gelatin (w/v), 0.05 percent MP40 or Triton X-100 (w/v)) per square cm of paper containing an appropriate dilution of prorennin antiserum and incubated for 4 hours at 4° C. The paper was then rinsed briefly with water and washed with NET buffer for 2 hours at room temperature, rinsed with water, blotted dry and incubated at room temperature for 1.5 hours in the presence of NET buffer containing $^{125}$I labeled protein A (0.25 μCi per gel lane) (Protein A is an antibody binding protein isoluted from Staphylcocus aureus.). The paper was then rinsed with water, and exposed to X-ray films with intensifying screens at 70° C. The presence of prorennin at a molecular weight of 40,000 daltons was confirmed.

c.5 Construction of pR1A

Modification to convert pRIA into an improved expression plasmid pR1A is outlined in FIG. 1B. Such modification altered the region between the Shine-Dalgarno sequence (which participates in ribosome binding) and the start codon (ATG).

In plasmid polyA-Xba, the region downstream from the trp promoter has had a sequence of bases added which results in a string of A's between an additional, newly created Shine-Dalgarno sequence on the one hand and an Xba I site on the other. This permits the vector to be cut at the Xba I site, and treated with S1 nuclease to remove the resulting "sticky end". When this end is ligated to a piece of DNA containing a start codon at or within a few bases of its 5' end, a favorable ribosome binding site is created. (The polyA-Xba plasmid is prepared as described herein.)

A sequence of operations which will accomplish this (diagrammed in FIG. 1B) is then as follows:

The plasmid polyA-Xba was cleaved as previously described, using the enzyme Xba I. The digest was EtOH precipitated, and resuspended in S1 buffer (100 μl per fragments from 25 μg of plasmid). S1 enzyme (5 units of BRL S1 nuclease) was added, the reaction mixture incubated at 12 degrees for 30 minutes, and quenched by extraction three times with phenol-chloroform. (The pH of the reaction mixture was adjusted (by adding 10 μl of 1M tris, pH 8) to improve the yield of the extraction.) The DNA was ethanol precipitated cleaved with Pst I, and the larger piece purified by gel electrophoresis.

The prorennin gene was conveniently prepared for insertion in 2 pieces. pR1 (or another plasmid containing the desired sequence) is cleaved with Kpn I and Pst I and the piece containing the 3' (back) end of the gene purified.

A second piece containing the 5' (front) end of the gene with the start codon at or near the end of the piece was prepared from pR1 by EcoRI cleavage, S1 nuclease treatment, Kpn I cleavage, and gel purification.

The three fragments were then ligated using the standard procedure described above. The S1 nuclease treatments described led to a distribution of products with sequences that end within 1 or 2 bases of the sequence end that would result from exact removal of the "sticky end". Hence, a distribution of ligation products with related, favorable ribosome binding site sequences results. From these, one with the sequence dGGGTATC-TAGGAAAAAAAATATG was chosen and was designated pR1A.

(The plasmid p poly A-Xba was constructed as follows: First, an intermediate plasmid was prepared by a three way legation involving fragments from two interferon plasmids and a piece of synthetic DNA. The plasmid pLeIF-AD trp (U.S. application Ser. No. 205,579 filed Nov. 10, 1980) was successively cleaved with Xba I and Pst I and the large fragment isolated on gel. The plasmid pIFNγ trp 48-13 (U.S. application Ser. No. 312,489 filed Oct. 19, 1981) was cleaved with Ava II and Pst I, and the 1000 bp fragment isolated. The DNA fragment

CTAGATGTGTTATTGTCAG
TACACAATAACAGTCCTG (with Xba I and Ava II sites at either end) was synthesized as described above. Ligation of the three pieces with T4 using standard procedures gave the intermediate plasmid pXba-IFNγ-1.

Plasmid pXba-IFNγ-1 was cleaved with Xba I, treated with alkaline phosphatase, and ligated to the synthetic fragment;

CTAGG(A)$_8$T
C(T)$_8$AGATC, to give p poly A-Xba.)

c.6 Construction of pR1X

Figure 1C:
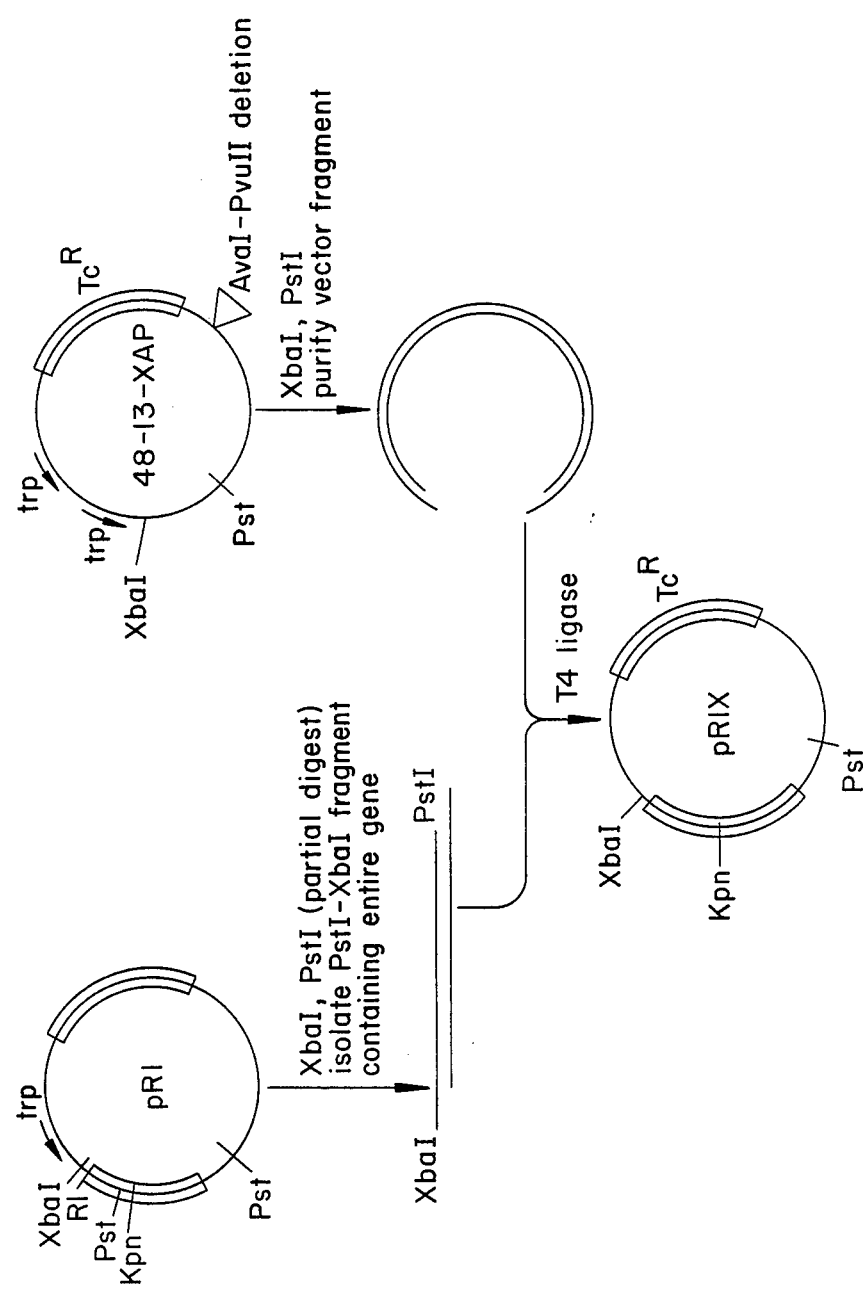
FIG. 1C is a schematic of the construction of plasmid pR1X.
Figure 10:
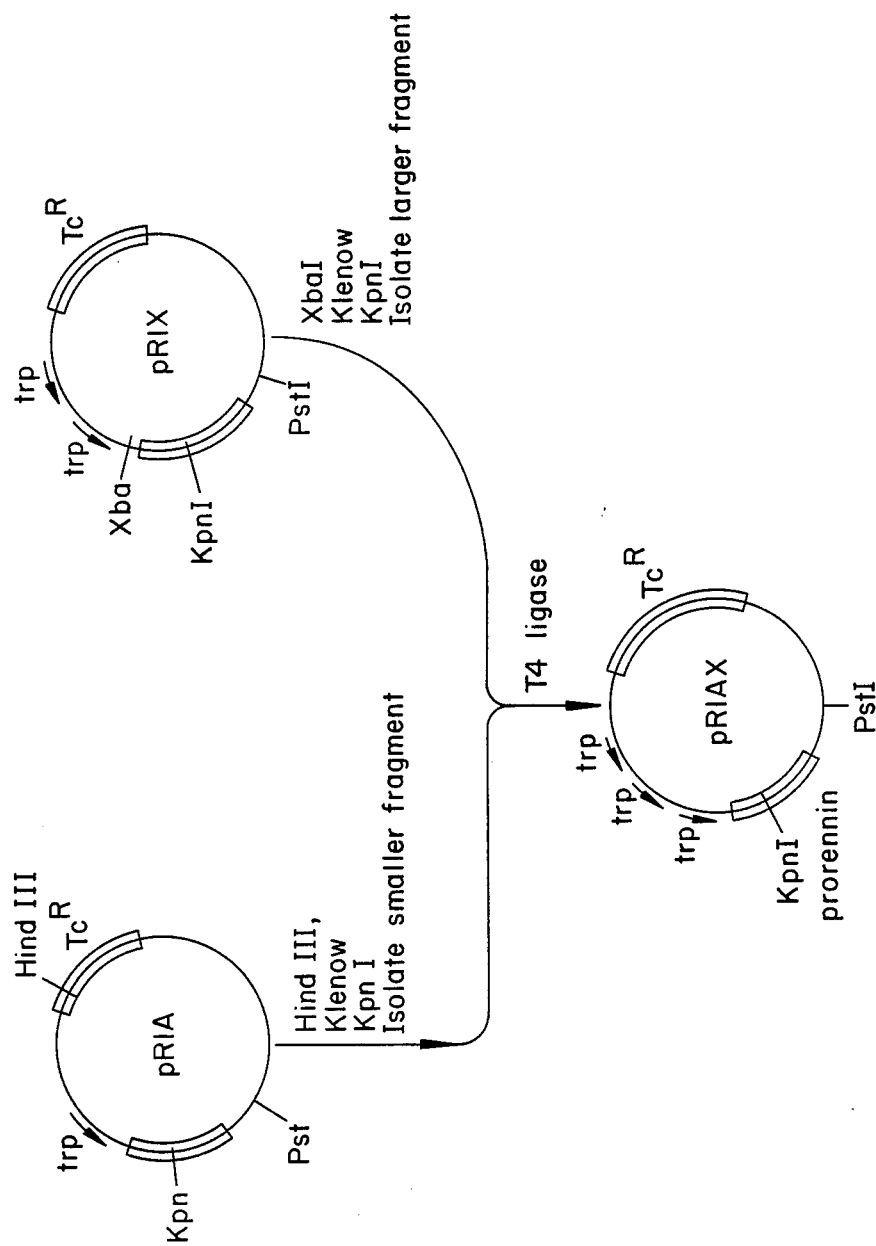

Modification to convert pR1 into another improved expression plasmid, pR1X, is outlined in FIG. 1C. The modification consists of excising the prorennin gene from pR1 in a single piece and inserting that gene into the expression vector, 48-13-XAP. (The plasmid gamma-48-13-XAP was prepared from pγIMM (supra) by deletion of the Ava I-Pvu II sequence.

The expression vector 48-13-XAP differs from that used to construct pR1 in two respects. First, a second trp promoter-operator sequence has been placed in tandem behind the first. Second, the XAP deletion (in which the region of pBR322 between its unique Ava I and PVU II sites has been deleted) has been constructed in this vector, resulting in an-increased number of plasmid copies in each host cell.

The plasmid 48-13-XAP was cleaved, at its unique Xba I and Pst I sites, and the larger resulting piece purified.

The plasmid pR1 was cleaved at its unique Xba I site and partially cleaved with Pst I to obtain the Xba I-Pst I piece containing the entire prorennin coding sequence and purified by gel purification.

These two pieces were ligated as previously described to obtain pR1X.

c.7 Construction of pR1AX

The plasmid used to produce prorennin for testing, pR1AX, was an improved expression vector obtained by modifying the plasmids pR1A and pR1X, described above, in the way diagrammed in FIG. 1D and described below:

Plasmid pR1A was cleaved with Hind III, and blunt ended by treating with DNA polymerase I Klenow fragment. (25 μg of cut plasmid DNA was incubated in 200 μl of a suitable buffer in the presence of ¼ mM of each deoxynucleotide and 10 units of New England Biolabs Klenow fragment at 37° for extraction and EtOH precipitation, as previously described.) The plasmid so treated was then digested with Kpn I and the piece containing the improved ribosome binding site, as well as a promoter copy and the 5' end of the prorennin coding sequence, was isolated on the gel.

The plasmid pR1X was digested at its unique Xba I site and treated with Klenow fragment as described above for the preparation of the pR1A-derived fragment. The plasmid DNA was then cleaved with Kpn I and the larger piece, containing the 3' end of the prorennin coding sequence, as well as the XAP deletion and 2 trp promoter copies, was isolated by gel purification.

These two fragments, each having one blunt end and one end derived from Kpn I digestion were ligated as previously described to obtain the plasmid pR1AX.

c.8 Production and Purification of Prorennin from *E. coli*

In a manner similar to that set forth in paragraph D.1.c.4 for pR1, *E. coli* K12 strain 3110 was transfected with pR1AX, and grown under conditions which favor the production of prorennin.

432 g of *E. coli* K12 (W3110/pR1AX) cell paste (killed by inactivating the culture medium 0.5 hr. at room temperature with 0.25 percent phenol 0.25 percent toluene), was harvested from 10 liters of culture medium and suspended in a total volume of 3 l of 50 mM Tris pH 7.5, 5 mM EDTA and 6 g of lysozyme, using a Tekmar homogenizer. The resulting suspension containing 19.6 mg/ml protein was passed through a Manton Gaulin four times at 6,000 psi. The refractile bodies were separated from host cell protein material by centrifugation at 4,000×g for 30 min. in a GS-3 rotor. The pellet was resuspended in 2 l of 50 mM Tris, pH 7.5, 5 mM EDTA using the Tekmar and repelleted as above.

The pellet was dissolved after overnight storage at 4° C. in a total volume of 632 ml of 6M guanidine-HCl and 50 mM Tris, pH 8.0 using the Tekmar homogenizer. Membranous material was removed by centrifugation at 5,000×g for 10 min. in a GSA rotor and the resulting solution was 25.0 mg/ml in protein (total 15.8 g). To the supernatant, 63.2 ml of a solution which is 200 mg/ml $Na_2SO_3$ and 100 mg/ml $Na_2S_4O_6$ was added and the resulting solution was incubated exactly 4 hours at room temperature. The sulfonating reagents and guanidine-HCl were removed by diafiltration into 5M urea (freshly deionized) and 50 mM Tris pH 7.5. The progress of diafiltration was monitored by pH and conductivity of the solution and was shown to be complete in 5 hours.

The diafiltered material was loaded onto a 10×35 cm DE-52 column equilibrated with 50 mM Tris pH 7.5 and 5M urea (freshly dionized) at a flow rate of 750 ml/h. The column was washed overnight at 500 ml/h. During the wash, a large void peak was eluted which has been shown in previous-column runs to contain very little or no prorennin. After 6½ hours (3.5 l of wash), a linear gradient of 0–0.15M NaCl with a total volume of 16 l was run at a rate of 1 l/h. The bulk of the prorennin was eluted at approximately 0.070M NaCl as shown by OD 280 and these fractions were shown to have only one other contaminating protein with a molecular weight of slightly less than 30K. The front end fractions contained several other contaminants of both higher and lower molecular weight.

The prorennin peak fractions comprising the $OD_{280}$ maximum and subsequent fraction to the end of the peak (see FIG. 2) were pooled, (volume=1,800 ml), and the pool diafiltered into 50 mM Tris pH 8.5 and 5M urea (freshly deionized). Sufficient reduced glutathione (GSH) and GSSG were added to make the final concentrations 1.0 mM and 0.1 mM, respectively, and the solution incubated overnight.

The urea was then removed using extensive dialysis into 50 mM Tris pH 8.0 and 0.1 mM GSH with three changes of buffer after 12 hour intervals (80 l/change).

The dialysate was then concentrated 4× to 500 ml and contained 11 mg/ml or 5.5 g of total protein as determined by biuret.

EXAMPLE 2

Milk Clotting Activity of Purified Prorennin Derived Enzyme

A. Skim Milk 5 ml aliquots of the prorennin dialysate concentrate prepared in Example 1 were activated by adding 0.5 ml of 0.45N HCl to give a pH of approximately 2, and incubating for 1 hour at 30° C. Skim milk was prepared by adding 1 g of dry milk (milk powder skim, U.S. Biochemical Corp, NDC12894) into 10 ml of 100 mM NaOAc, pH 6.0, 10 mM $CaCl_2$, and homogenizing 50 times. The milk was preincubated at 30° C.

Enzyme samples were prepared as follows:

5 μl and 10 μl of activivated prorennin were added to 95 μl and 90 μl respectively of 100 mM sodium acetate, pH 6.0, 10 mM $CaCl_2$, and preincubated at 30° C.

A 1:30 dilution of Marshall rennet (Miles laboratories) was also prepared as a control.

100 μl of each enzyme preparation was added to a 900 μl aliquot of skim milk at 30° C., and clotting time recorded. Units of enzyme activity were calculated using the equation: $198/(sec-8) \times$ dilution factor=units per ml of undiluted enzyme i.e., the original dialyzate or the undiluted rennet.

The sample containing 5 μl of activated prorennin gave 202.6 units per ml of original dialysate, however that containing 10 μl of prorennin 380.8 units per ml and that of the control gave 1563 units per ml of undiluted Rennet (compared to the label value of 1600 unit/ml). A subsuquent 1:20 dilution of the enzyme was also tested, and confirmed a value of the prorennin preparation at 374 units per ml of the dialysate.

B. Pasteurized Milk

The procedure is similar to that in paragraph A. The dialysate containing prorennin prepared in Example 1 was activated by mixing 19.6 ml of 0.45N HCl with 196 ml of dialysate, to give pH 2, and incubating at 30° for 45 minutes.

To test clotting, to two 10 ml portions of pasteurized milk were added respectively, 1.98 μl of undiluted Marshall rennet and 8.5 μl of the dialysate. The respective clotting times were 18 min. and 9 min.

EXAMPLE 3

Determination of Cheese Yield 5 batches, 7,000 g each, of milk containing 3.95 percent fat and 12.57 percent solids were preincubated, each with 16 g of D-gluconic acid lactone for 30 minutes at 30° C. 2.5 ml of activated microbial prorennin as prepared in Example 2B were added to batches 3, 4, and 5. Sufficient Marshall rennet so that the milk coagulates in approximately 25 minutes was added to batches 1 and 2. After 25 minutes, the curd was cut, heated to 102° F. over the next 30 minutes, drained of whey, pressed and weighed. The results are shown in the table below:

| Batch No. | percent yield ( g dry matter / 100 g milk ) | percent yield wet (corrected for std moisture) | actual percent yield of wet curd |
|---|---|---|---|
| 1 | 6.76 | 11.08 | 11.92 |
| 2 | 6.72 | 11.02 | 11.85 |
| 3 | 6.82 | 11.18 | 12.05 |
| 4 | 6.95 | 11.39 | 11.95 |

-continued

| Batch No. | percent yield $\left(\dfrac{\text{g dry matter}}{100 \text{ g milk}}\right)$ | percent yield wet (corrected for std moisture) | actual percent yield of wet curd |
|---|---|---|---|
| 5 | 6.70 | 10.98 | 11.52 |

In the above table, yields are given in the following terms: Column 1 gives percent yield of dry matter with respect to whole milk. Column 2 is calculted by dividing the values in Column 1 by 0.61; it gives the percent yield as wet weight that would be expected if the "usual" amount of moisture is present. Column 3 gives the percent wet weight actually obtained. Of course, the actual wet weight yield of cheese will be greater the higher the moisture content of the resulting cheese. Typically, cheese made in a process of this kind by rennent coagulation will contain a moisture content of approximately 39 percent. Accordingly, in column 2 the percentage of wet weight is calculated assuming a 39 percent moisture content in the product. This allows comparison with yields obtained in commerical processes wherein these moisture contents are obtained. Typically, cheddar cheese prepared from 3.5 percent fat milk containing a moisture of 39 percent will give a wet yield of 9.7 percent. All of the samples in the above trial contained approximately 11 percent yield, which is sufficiently higher than the ordinarily obtained due to the higher fat content of the milk. As seen above, the commercial rennet and the microbially produced activated prorennin gave comparable yields, but that for the commercially produced rennet was slightly lower than that in batch 3. (The yields obtained in batches 4 and 5 are not really comparable as the clotting time was appreciably less than ideal in these trials.) Also, the moisture of the cheese produced was somewhat higher then the 39 percent typically obtained, ranging from approximately 43 to 44 percent in the first three batches to approximately 42 percent in batches 4 and 5.

While the yields as determined by batch 3 are not appreciably higher then those in the control, it appears that some improvement may have been effected. It is to be noted in this regard, that even slight increases in yield are regarded as significant. This is because of the large scale involved in commercial processes where only a small improvement results in a large economic benefit. For example, in a paper entitled "Effect of Milk Clotting Enzymes on Cheese Yield" presented at the Cheese Industry Conference in Logan, Utah on Sept. 1, 1982 by Dr. Robert L. Sellers, it is pointed out that differences of even hundreths of a percentage point are significant. For example, wet weight yields of 9.947 percent compared favorably with yields 9.909 percent for various commerical rennet products.

EXAMPLE 4

Manufacture of Cheese using Microbial Rennin

Milk, 3.95 percent in fat, produced at the University of Kentucky Dairy was pasteurized at 145° F. for 30 minutes and then cooled to 36° F. for overnight storage. The milk was then warmed to 85° F. and placed in vats in lots of 400 lbs per vat.

4 g of Chris Hansen starter culture CH60 was added to each vat, and the mixture allowed to stand at 86° F. for one hour. Calf rennin as prepared in Example 1 and activated as in Example 2, was then added over a period of 25–30 minutes to batches 2 and 3. Marshall rennet was added to batch 1. During this time, curd was formed which was cut at the end of the 30 minutes with $3\frac{1}{8}''$ knives, and then allowed to heal for 15 minutes. The curd temperature was then increased to 102° F. over a 30 minute period and maintained at that temperature, with agitation until the pH reached 6.1.

Whey was then drained, and the curd allowed to mat with turning every 10-15 minutes. When pH of 5.8 was reached, the curd was stacked two high, and at pH 5.6 it was stacked three high. When the pH reached 5.4, the curd was mulled, salted, hooped, and pressed.

After a 30 minute pressing, hoops were dressed and pressed for an additional 16 hours, and the cheese packaged in a cryovac saran bag, S-11 which was then heat shrunk in boiling water. The bagged cheese was then stored in a 40° cooler.

The results are shown in the following table:

| Batch | Amt added | Clotting time | Percent dry wt. yield (g dry matter/ 100 g milk | Percent wet wt. curd corrected for std moisture | Actual percent yield of wet curd | Grade |
|---|---|---|---|---|---|---|
| 1 | 40 ml | 25 min | 6.72 | 11.02 | 10.94 | 11/15 |
| 2 | 84 ml | 23 min | 7.00 | 11.46 | 11.44 | 13/15 |
| 3 | 90 ml | 11 min | 6.71 | 10.99 | 11.00 | 12/15 |

As the table shows, reasonable clotting times are given only by batches 1 and 2. Again the yield, whether based on a standard 39 percent moisture content, or on the actual amount of moisture, was higher in the case of the microbially prepared, activated prorennin. In any case, comparable yields were obtained.

Perhaps more important are the results of the tests on the quality of the cheese produced. These are expressed as "grade" in the table, wherein the evaluation on a scale of 15, as judged by two experienced cheese tasters, is tabulated. The scale is structured on a standard set of criteria including taste, texture, color, and aroma which is promulgated by the USDA and in common use in the industry. As the table shows, the highest quality cheese of the three batches was batch number 2, prepared with the proper clotting time, using the microbial rennet. That cheese, while somewhat pasty, was graded higher than the products of batches of 1 and 3.

It may further be remarked that in all three batches, the assay with respect to bacterial counts was entirely analogous. In the pasteurized milk before treating with starter, the "plate count agar" test which is designed to count total bacteria, yielded in the range of $1\frac{1}{2}$ to 3 times $10^2$ total bacteria, while the violet red bile medium, designed to detect coliform gave less than 10 microorganisms per ml of milk. After starter is added, of course, the total count increases as this constitutes an addition of bacteria to aid in ripening the resulting cheese. In all three batches, total bacterial counts as measured on "all purpose Tween" medium and "Ellikers" medium were in the range of 1 to 2 times $10^7$ cells per ml. Approximately 4 to 6 times $10^5$ total bacteria cells per ml remain in the whey after the curd had been separated in all cases whether by "all purpose Tween" or Ellikers. Again, the coliform count in all cases was less than ten cells per ml.

In summary, the results of cheese production on a commercial scale—i.e. 400 lb. lots, is comparable with if not superior to, commercial calf rennet for microbially produced activated prorennin.

What is claimed is:

1. A process for the production of active rennin from preprorennin, prorennin or rennin which has been produced in a recombinant microbial host cell in the form of an insoluble refractile body, which process comprises:
   (a) rupturing the recombinant microbial host cell;
   (b) isolating insoluble refractile bodies from the recombinant host cell;
   (c) solubilizing the refractile bodies; and
   (d) recovering active rennin.

2. A process according to claim 1 which further comprises converting the preprorennin or prorennin to active rennin.

3. A process according to claim 1 wherein the preproprennin, prorennin or rennin is solubilized in guanidine at a concentration of about 1–9M.

4. The process according to claim 3 wherein the concentration of the solution is 6–8M.

5. A process according to claim 1 wherein the refractile body is isolated by centrifugation.

6. A process according to claim 1 wherein a sulfatolysis agent is added to the solubilized refractile body.

* * * * *